(12) United States Patent
Maurer et al.

(10) Patent No.: US 6,911,416 B2
(45) Date of Patent: Jun. 28, 2005

(54) SUBSTITUTED N-BENZOYL-N' (TETRAZOLYLPHENYL)-UREAS AND THEIR USE AS PEST CONTROL AGENTS

(75) Inventors: Fritz Maurer, Monheim (DE); Christoph Erdelen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 193 days.

(21) Appl. No.: 10/275,829

(22) PCT Filed: May 2, 2001

(86) PCT No.: PCT/EP01/04899

§ 371 (c)(1),
(2), (4) Date: Nov. 8, 2002

(87) PCT Pub. No.: WO01/85705

PCT Pub. Date: Nov. 15, 2001

(65) Prior Publication Data

US 2003/0187043 A1 Oct. 2, 2003

(30) Foreign Application Priority Data

May 12, 2000 (DE) .......................................... 100 23 430

(51) Int. Cl.$^7$ ...................... A01N 43/647; C07D 257/00
(52) U.S. Cl. ...................................... 504/261; 548/253
(58) Field of Search ............................. 504/261; 548/253

(56) References Cited

U.S. PATENT DOCUMENTS

| | | | |
|---|---|---|---|
| 3,838,126 A | 9/1974 | Wagner | 260/256.4 F |
| 4,333,874 A | 6/1982 | Nickel et al. | 242/153 |
| 4,913,726 A | 4/1990 | Levitt | 71/92 |
| 4,950,678 A | 8/1990 | Carney et al. | 514/340 |

FOREIGN PATENT DOCUMENTS

| | | |
|---|---|---|
| DE | 933 581 | 9/1955 |
| DE | 37 32 541 | 4/1989 |
| EP | 0 056 124 | 7/1982 |
| WO | 94/29268 | 12/1994 |

OTHER PUBLICATIONS

Chem. Ind., 37, (month unavailable) 1985, pp. 730–732, Harry R. Ungerer, "Schiffsfarben—eine Spezialitat der seenahen Lackindustrie".

Synthesis (month unavailable) 1998, pp. 910–914, Kiyoto Koguro, Toshikazu Oga, Sunao Mitsui, Ryozo Orita, "Novel Synthesis of 5-Substituted Tetrazoles from Nitriles".

Nakagawa Y et al: "Quantitative Structure–Activity Studies of Benzoylphenylurea Larvicides V. Substituted Pyridyloxphenyl and Related Derivatives" Pesticide Biochemistry and Physiology, Academic Press, US, Bd. 30, Nr. 1, Jan. 1988 (1988–01), Seiten 67–78, XP001014578 ISSN: 0048–3575 das ganze Dokument.

Database Beilstein 'Online!Beilstein Institute for Organic Chemistry, Frankfurt/Main DE: Database accession No. 1109095 (BRN) XP002176678 4–Methyl–2–(1H–tetrazol–5–yl)–anilin & Chem. Heterocycl. Compd. (Engl. Transl.), 1970, 6, 266.

Database Beilstein 'Online!Beilstein Institute for Organic Chemistry, Frankfurt/Main, DE; Database accession No. 139593 und 139601 (BRN) XP002176679 3–und 4–(1H–tetrazol–5–yl)anilin & J. Org. Chem. 1959, 24, 1044.

Database Chemcats 'Online!Chemical Abstracts Service, Columbus, Ohio, US; Apr. 26, 2001, Database accession No. 2001:111457 XP 002176680 2–Fluor–4–(1H–tetrazol–5–yl)–anilin.

Database Chemcats 'Online Chemical Abstracts Service, Columbus, Ohio, US' Apr. 26, 2001 Database accession No. 2001:663244 XP002176681 2–Fluor–5–(1H–tetrazol–5–yl)–anilin.

Ursini A et al: "Synthesis and Sar of New 5–Phenyl–3–Ureldo–1,5–Benzodiazepines as Cholecystokinin–B Receptor Atagonists" Journal of Medicinal Chemistry, American Chemical Society. Washington, US, Bd. 43, Nr. 20, Sep. 19, 2000, Seiten 3596–3613, XP000999557 ISSN: 0022–2623 Tabelle 2, Verbindung 38; Schema 3.

Primary Examiner—Deborah C. Lambkin
Assistant Examiner—Sonya Wright
(74) Attorney, Agent, or Firm—Richard E. L. Henderson; Raymond J. Harmuth

(57) ABSTRACT

The present invention relates to new substituted N-benzoyl-N'-(tetrazolylphenyl)-ureas of the formula (I)

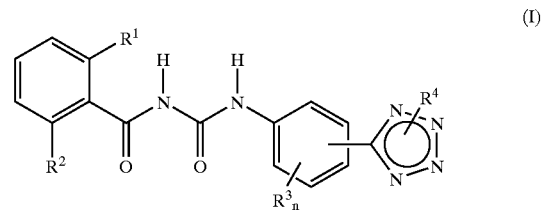

(I)

in which
$R^1$, $R^2$, $R^3$, $R^4$ and n are as stated in the description, to processes for their preparation, and to their use as pesticides.

8 Claims, No Drawings

SUBSTITUTED N-BENZOYL-N'-(TETRAZOLYLPHENYL)-UREAS AND THEIR USE AS PEST CONTROL AGENTS

The present invention relates to new substituted N-benzoyl-N'-(tetrazolylphenyl)-ureas, to processes for their preparation and to their use as pesticides.

It has been disclosed that certain substituted N-(benzoyl)-N'-(heterocyclylphenyl)-ureas have insecticidal and acaricidal properties (cf., for example, DE-A 37 32 541, EP-A 0 242 322 or U.S. Pat. No. 4,950,678). However, the action of these compounds is not always entirely satisfactory, in particular when low active compound concentrations and application rates are used.

There have been found new substituted N-benzoyl-N'-(tetrazolylphenyl)-ureas of the formula (I)

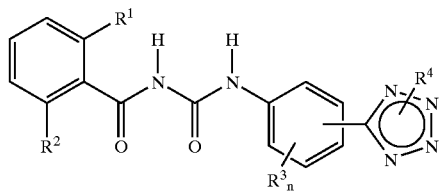

(I)

in which
R¹ represents halogen,
R² represents hydrogen or halogen,
R³ represents halogen, alkyl or halogenoalkyl,
n represents 0, 1 or 2 and
R⁴ represents hydrogen, optionally substituted alkyl, optionally substituted alkenyl, alkoxyalkyl, alkoxycarbonylalkyl, alkylcarbonyloxyalkyl, alkylsulphonyl, diaminocarbonyl; in each case optionally substituted aryl, arylalkyl or arylsulphonyl; in each case optionally substituted cycloalkyl or cycloalkylalkyl or in each case optionally substituted heterocyclyl or heterocyclylalkyl.

Furthermore it has been found that the substituted N-benzoyl-N'-(tetrazolylphenyl)-ureas of the formula (I) are obtained when a) benzoyl isocyanates of the formula (II)

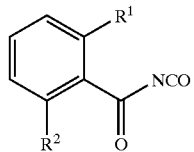

(II)

in which
R¹ and R² are as stated above
are reacted with tetrazolylanilines of the formula (III)

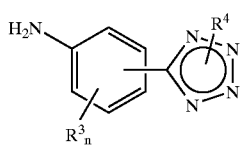

(III)

in which
R³, n and R⁴ are as stated above
in the presence of a diluent; and, b) if appropriate, the resulting compounds of the formula (Ia) according to the invention

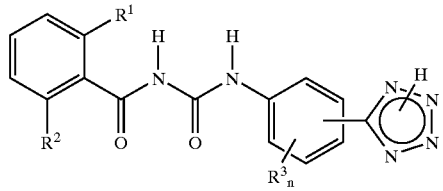

(Ia)

in which
R¹, R², R³ and n are as stated above
are reacted with compounds of the formula (IV)

$$E-R^{4-1}$$ (IV)

in which
$R^{4-1}$ is as stated above for R⁴, with the exception of hydrogen, and
E represents an anionic leaving group
in the presence of a diluent and, if appropriate, in the presence of an acid acceptor.

Finally, it has been found that the new substituted N-benzoyl-N'-(tetrazolylphenyl)-ureas of the formula (I) have potent biological properties and that they are suitable especially for controlling animal pests, in particular insects, arachnids and nematodes, which are found in agriculture, in forests, in the protection of stored products and materials, and in the hygiene sector.

Formula (I) provides a general definition of the substituted N-benzoyl-N'-(tetrazolylphenyl)-ureas according to the invention.

Preferred substituents or ranges of the radicals given in the formulae stated hereinabove and hereinbelow are illustrated in the following text:

R¹ preferably represents fluorine or chlorine.
R² preferably represents hydrogen, fluorine or chlorine.
R³ preferably represents fluorine, chlorine, bromine, $C_1$–$C_4$-alkyl or $C_1$–$C_4$-halogenoalkyl.
n preferably represents 0, 1 or 2.
R⁴ preferably represents hydrogen, $C_1$–$C_6$-alkyl, $C_1$–$C_4$-halogenoalkyl, $C_2$–$C_4$-alkenyl, $C_2$–$C_4$-halogenoalkenyl, $C_1$–$C_4$-alkoxy-$C_1$–$C_4$-alkyl, $C_1$–$C_4$-alkoxy-carbonyl-$C_1$–$C_4$-alkyl, $C_1$–$C_4$-alkyl-carbonyloxy-$C_1$–$C_4$-alkyl; $C_1$–$C_4$-alkylsulphonyl, di-($C_1$–$C_4$-alkyl)-aminocarbonyl, or represents phenyl, benzyl or phenylsulphonyl, each of which is optionally monosubstituted to trisubstituted by identical or different substituents from the series consisting of halogen, nitro, cyano, $C_1$–$C_4$-alkyl, $C_1$–$C_4$-alkoxy, $C_1$–$C_4$-halogenoalkyl and $C_1$–$C_4$-halogenoalkoxy; or represents cyclopentyl, cyclohexyl or cyclohexyl-$C_1$–$C_2$-alkyl, each of which is optionally monosubstituted to trisubstituted by identical or different substituents from the series consisting of $C_1$–$C_4$-alkyl and $C_1$–$C_4$-alkoxy, or represents five- or six-membered heterocyclyl or five- or six-membered heterocyclyl-$C_1$–$C_2$-alkyl, each of which has one or two heteroatoms, such as N, O or S atoms, and each of which is optionally monosubstituted to trisubstituted by identical or different substituents from the series consisting of $C_1$–$C_4$-alkyl and $C_1$–$C_4$-alkoxy.

$R^1$ especially preferably represents fluorine or chlorine.

$R^2$ especially preferably represents hydrogen, fluorine or chlorine.

$R^3$ especially preferably represents fluorine, chlorine, methyl or trifluoromethyl.

n especially preferably represents 0, 1 or 2.

$R^4$ especially preferably represents hydrogen, $C_1$–$C_6$-alkyl, $C_2$–$C_4$-alkenyl, $C_1$–$C_2$-halogenoalkyl or $C_2$–$C_4$-halogenoalkenyl having in each case 1 to 3 identical or different halogen atoms from the series consisting of fluorine, chlorine and bromine; $C_1$–$C_4$-alkoxy-$C_1$–$C_2$-alkyl, $C_1$–$C_4$-alkoxy-carbonyl-$C_1$–$C_2$-alkyl, $C_1$–$C_4$-alkyl-carbonyloxy-$C_1$–$C_2$-alkyl, $C_1$–$C_2$-alkylsulfonyl, di-($C_1$–$C_2$-alkyl)-aminocarbonyl; or represents phenyl, benzyl or phenylsulphonyl, each of which is optionally monosubstituted to trisubstituted by identical or different substituents from the series consisting of halogen, nitro, cyano, $C_1$–$C_4$-alkyl, $C_1$–$C_4$-alkoxy, $C_1$–$C_2$-halogenoalkyl and $C_1$–$C_2$-halogenoalkoxy having in each case 1 to 3 identical or different halogen atoms from the series consisting of fluorine, chlorine and bromine; or represents cyclopentyl, cyclohexyl or cyclohexylmethyl, each of which is optionally monosubstituted to trisubstituted by identical or different substituents from the series consisting of $C_1$–$C_4$-alkyl and $C_1$–$C_4$-alkoxy; or represents tetrahydrofuranyl, tetrahydrofuranylmethyl, tetrahydropyranyl or tetrahydropyranylmethyl, each of which is optionally monosubstituted to trisubstituted by identical or different substituents from the series consisting of $C_1$–$C_4$-alkyl and $C_1$–$C_4$-alkoxy.

$R^1$ very especially preferably represents fluorine or chlorine.

$R^2$ very especially preferably represents hydrogen, fluorine or chlorine.

$R^3$ very especially preferably represents fluorine, chlorine or trifluoromethyl.

n very especially preferably represents 0, 1 or 2.

$R^4$ very especially preferably represents hydrogen; methyl, ethyl, n- or i-propyl, n-, i-, s- or t-butyl; 1-ethyl-1-methyl-propyl, 1,1-dimethylpropyl, 2-methyl-2-propenyl, fluoromethyl, difluoromethyl, trifluoromethyl, 1,1-difluoroethyl, 2,2,2-trifluoroethyl, 3,4,4-trifluoro-3-butenyl, 4,4-difluoro-3-butenyl, methoxymethyl, ethoxymethyl, methoxyethyl, ethoxyethyl, methoxycarbonylmethyl, ethoxycarbonylmethyl, methoxycarbonylethyl, ethoxycarbonylethyl, methylcarbonyloxymethyl, ethylcarbonyloxymethyl, methylcarbonyloxyethyl, ethylcarbonyloxyethyl, methylsulphonyl, ethylsulphonyl, dimethylaminocarbonyl, methylethylaminocarbonyl, diethylaminocarbonyl, or represents phenyl, benzyl or phenylsulphonyl, each of which is optionally monosubstituted or disubstituted by identical or different substituents from the series consisting of fluorine, chlorine, bromine, methyl, methoxy, trifluoromethyl or trifluoromethoxy; or represents cyclohexyl, tetrahydropyranyl or tetrahydropyranylmethyl, each of which is optionally monosubstituted or disubstituted by identical or different substituents from the series consisting of methyl, ethyl, methoxy or ethoxy.

$R^1$ particularly represents fluorine or chlorine.

$R^2$ particularly represents hydrogen, fluorine or chlorine.

$R^3$ particularly represents fluorine, chlorine or trifluoromethyl.

n particularly represents 0, 1 or 2.

$R^4$ particularly represents hydrogen; methyl, ethyl, n- or i-propyl, n-, i-, s- or t-butyl; 1-ethyl-1-methyl-propyl, 1,1-dimethylpropyl, 2-methyl-2-propenyl, fluoromethyl, difluorimethyl, trifluorimethyl, 1,1-difluoroethyl, 2,2,2-trifluoroethyl, 3,4,4-trifluoro-3-butenyl, methoxycarbonylmethyl, ethoxycarbonylmethyl, methoxycarbonylethyl, ethoxycarbonylethyl or represents phenyl or benzyl, each of which is optionally substituted by bromine; or represents cyclohexyl which is substituted by methyl, or represents tetrahydropyranylmethyl or tetrahydropyranyl, methoxymethyl, ethoxymethyl, methoxyethyl, ethoxyethyl, methylcarbonyloxymethyl, ethylcarbonyloxymethyl, methylcarbonyloxyethyl, ethylcarbonyloxyethyl.

Preferred compounds of the formula (I) are those where the tetrazole on the phenyl ring is substituted in the 4-position.

Other preferred compounds of the formula (I) are those where the tetrazole on the phenyl ring is substituted in the 2-position.

Other preferred compounds of the formula (I) are those where the tetrazole on the phenyl ring is substituted in the 3-position.

The definitions of radicals or explanations given hereinabove or in preferred ranges apply to the end products and, analogously, to the starting materials and intermediates. These definitions of radicals can be combined with each other as desired, that is to say combinations between each of the preferred ranges are also possible.

Preferred in accordance with the invention are the compounds of the formula (I) in which a combination of the meanings given hereinabove as preferred (by preference) is present.

Especially preferred in accordance with the invention are the compounds of the formula (I) in which a combination of the meanings given hereinabove as especially preferred is present.

Very especially preferred in accordance with the invention are the compounds of the formula (I) in which a combination of the meanings given hereinabove as very especially preferred is present.

Very particularly preferred in accordance with the invention are the compounds of the formula (I) in which a combination of the meanings given hereinabove as very particularly preferred is present.

In the definitions of radicals stated hereinabove and hereinbelow, hydrocarbon radicals such as alkyl—also in connection with heteroatoms such as alkoxy—are in each case straight-chain or branched, as far as this is possible.

If, for example, 2,6-difluorobenzoyl isocyanate and 1-methyl-5-(3-chloro-4-aminophenyl)-tetrazole are used as starting materials, the course of the reaction of process (a) according to the invention can be represented by the following formula scheme:

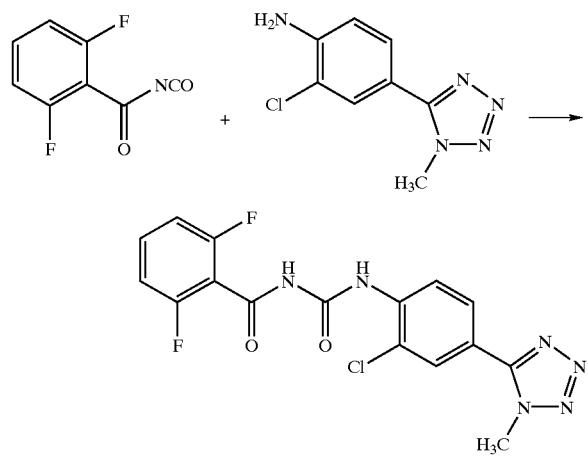

If, for example, N-(2,6-difluorobenzoyl)-N'-(2-chloro-4-tetrazol-5-yl-phenyl)-urea and 2-(4-methylsulphonylphenyl)-tetrahydropyran are used as starting materials, the course of the reaction of process (b) according to the invention can be represented by the following formula scheme:

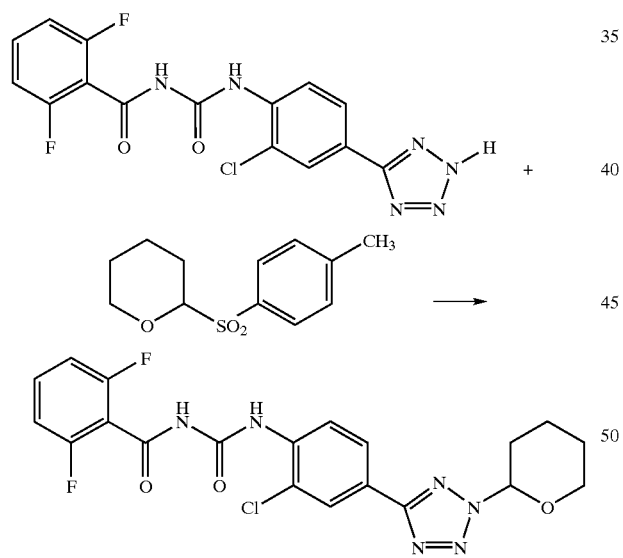

Formula (II) provides a general definition of the benzoyl isocyanates to be used as starting materials for carrying out process (a) according to the invention. The benzoyl isocyanates of the formula (II) are known and can be obtained by generally known methods.

Formula (III) provides a general definition of the tetrazolylanilines furthermore to be used as starting materials in process (a) according to the invention. Some of the tetrazolylanilines of the formula (III) are known (see, for example, Synthesis 1998, pp. 910–914).

The new tetrazolylanilines of the formula (III)

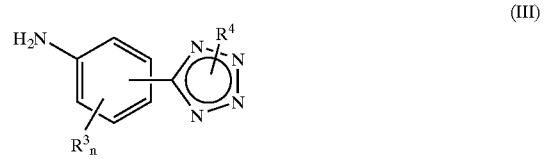

(III)

in which $R^3$ represents chlorine, fluorine, trifluoromethyl or methyl, n represents 1 or 2, $R^4$ is as stated above and the position of substitution of the tetrazole of the phenyl ring is in the 2-, 3- or 4-position, are also subject-matter of the present application.

Also subject-matter of the present application are compounds of the formula (III) in which n represents 0 and $R^4$ and the position of substitution of the tetrazole on the phenyl ring are as stated in the table.

| $R^4$ | Position of substitution of the tetrazole on the phenyl ring |
|---|---|
| 2-C(C$_2$H$_5$)$_2$<br>\|<br>CH$_3$ | 4 |
| 2-C(CH$_3$)$_2$<br>\|<br>C$_2$H$_5$ | 4 |
| 2-CHF$_2$ | 3 or 4 |
| 1-CHF$_2$ | 3 or 4 |
| H | 3 or 4 |
| 2-C$_4$H$_9$-t | 3 or 4 |

They can be obtained in the generally known manner by reacting, preferably under reflux, known aminobenzonitriles of the formula (V)

(V)

in which $R^3$ and n are as stated above with sodium azide and, for example, triethylamine hydrochloride in the presence of an inert solvent such as, for example, acetonitrile, dimethylformamide or toluene (cf. also the Preparation Examples) and, if appropriate, reacting the resulting tetrazolylanilines of the formula (IIIa)

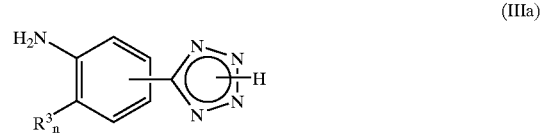

(IIIa)

in which

R³ and n are as stated above with compounds of the formula (IV) in accordance with process (b) according to the invention (cf. also the Preparation Examples).

Formula (IV) provides a general definition of the compounds to be used as starting materials for carrying out the process (b) according to the invention.

In this formula, E preferably represents chlorine, bromine, iodine, acetoxy, tosyl or mesyl.

The compounds of the formula (IV) are known and/or can be prepared in the known manner, if appropriate they may also be reacted further directly in situ (cf. also the Preparation Examples).

Processes (a) and (b) according to the invention are preferably carried out using diluents. Suitable diluents are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, dibutyl ether, glycol dimethyl ether, diglycol dimethyl ether, tetrahydrofuran and dioxane, ketones such as acetone, methyl ethyl ketone, methyl isopropyl ketone, or methyl isobutyl ketone, esters such as methyl acetate or ethyl acetate, nitriles such as, for example, acetonitrile or propionitrile, amides such as, for example, dimethylformamide, dimethylacetamide and N-methylpyrrolidone and dimethylsulphoxide, tetramethylene sulphone or hexamethylphosphoric triamide.

Acid acceptors which can be employed in process (b) according to the invention are all acid binders which can conventionally be used for reactions of this type. The following are preferably suitable: alkali metal hydrides and alkaline earth metal hydrides such as lithium hydride, sodium hydride, potassium hydride or calcium hydride, alkali metal hydroxides or alkaline earth metal hydroxides such as lithium hydroxide, sodium hydroxide, potassium hydroxide or calcium hydroxide, alkali metal carbonates, alkali metal hydrogencarbonates, alkaline earth metal carbonates or alkaline earth metal hydrogencarbonates, such as sodium carbonate, sodium hydrogencarbonate, potassium carbonate, potassium hydrogencarbonate or calcium carbonate, alkali metal acetates such as sodium acetate or potassium acetate, alkali metal alkoxides such as sodium tert-butoxide or potassium tert-butoxide, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) or 1,4-diazabicyclo-[2,2,2]-octane (DABCO).

When carrying out processes (a) and (b) according to the invention, the reaction temperatures can be varied within a substantial range. In general, the process is carried out at temperatures between 0° C. and 100° C., preferably at temperatures between 10° C. and 80° C.

In general, processes (a) and (b) according to the invention are carried out under atmospheric pressure. However, it is also possible to carry out the processes under elevated or reduced pressure.

To carry out processes (a) and (b) according to the invention, the starting materials required in each case are generally employed in approximately equimolar amounts. However, it is also possible to use one of the two components employed in each case in a larger excess. Work-up is carried out in each case by customary methods in the processes according to the invention (cf. the Preparation Examples).

When preparing compounds in which $R^4$ represents a tertiary alkyl radical, it is advantageous in some cases to react the compounds of the formula (Ia) or of the formula (IIIa) with tertiary alcohols in the presence of strong acids such as, for example, trifluoroacetic acid and/or sulphuric acid (cf. also the Preparation Examples).

The active compounds can be used for controlling animal pests, in particular insects, arachnids and nematodes, which are found in agriculture, in forests, in the protection of stored products and materials, and in the hygiene sector, while being well tolerated by plants and showing advantageous toxicity to warm-blooded species. They can preferably be used as crop protection agents. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus*, Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus*, Gryllotalpa spp., *Locusta migratoria migratorioides*, Melanoplus spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, Reticulitermes spp.

From the order of the Phthiraptera, for example, *Pediculus humanus corporis*, Haematopinus spp., Linognathus spp., Trichodectes spp., Damalinia spp.

From the order of the Thysanoptera, for example, *Hercinothrips femoralis, Thrips tabaci, Thrips palmi, Frankliniella accidentalis.*

From the order of the Heteroptera, for example, Eurygaster spp., *Dysdercus intermedius, Piesma quadrata, Cimex lectularius, Rhodnius prolixus*, Triatoma spp.

From the claorder of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp., Psylla spp.

From the order of the Lepidoptera, for example, *Pectinophora gossypiella, Bupalus piniarius, Cheimatobia*

*brumata, Lithocolletis blancardella, Hyponomeuta padella, Plutella xylostella, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Mamestra brassicae, Panolis flammea,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana,* Cnaphalocerus spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica, Lissorhoptrus oryzophilus.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Hylemyia spp., Liriomyza spp.

From the order of the Siphonaptera, for example, *Xenopsylla cheopis,* Ceratophyllus spp.

From the class of the Arachnida, for example, *Scorpio maurus, Latrodectus mactans, Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Hemitarsonemus spp., Brevipalpus spp.

The plant-parasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp., Bursaphelenchus spp.

The substances according to the invention can be employed particularly successfully for controlling plant-injurious insects, such as, for example, against tobacco bedworm (*Heliothis virescens*) caterpillars, mustard beetle (*Phaedon cochleariae*) larvae, diamond-backed moth (*Plutella xylostella*) caterpillars and fall army worm (*Spodoptera exigua* and *Spodoptera frugioerda*) caterpillars.

If appropriate, the compounds according to the invention can also be used as herbicides and microbicides, for example as fungicides, antimycotics and bactericides, using specific concentrations/application rates. If appropriate, they can also be used as intermediates or precursors for the synthesis of further active compounds.

All plant and plant parts can be treated in accordance with the invention. Plants in this context are taken to mean all plants and plant populations, such as desired and undesired wild plants or crop plants (including naturally occurring crop plants). Crop plants can be plants which can be obtained by conventional breeding and optimization methods, or by biotechnological and genetic engineering methods, or by combinations of these methods, including the transgenic plants and including the plant varieties which are capable, or incapable, of being protected by Plant Breeders' Rights. Plant parts are to be taken to mean all aerial and subterranean parts and organs of the plants, such as shoot, leaf, flower and root, examples mentioned being leaves, needles, stalks, stems, flowers, fruit bodies, fruit and seeds, and also roots, tubers and rhizomes. The plant parts also include harvested material and vegetative and generative propagation material, for example cuttings, tubers, rhizomes, offshoots and seeds.

Treatment according to the invention of the plants or plant parts with the active compounds is performed either directly or by exposure of the environment, habitat or store by the customary treatment methods, for example by dipping, spraying, releasing vapour, fogging, spreading, painting on, and, in the case of propagation material, in particular seeds, furthermore by coating with one or more coats.

As already mentioned above, all plants and their parts can be treated in accordance with the invention. In a preferred embodiment, plant varieties and plant species which are either found wild or obtained by conventional biological breeding methods, such as hybridization or protoplast fusion, and the parts of these plant species and plant varieties are treated. In a further preferred embodiment, transgenic plants and plant varieties which have been obtained by genetic engineering methods, if appropriate in combination with conventional methods (Genetically Modified Organisms) and their parts are treated. The term "parts" or "parts of plants" or "plant parts" has been explained hereinabove.

Plants which are treated in accordance with the invention are especially preferably plants of the plant varieties which are in each case commercially available or in current use. Plant varieties are to be understood as meaning plants with particular traits which have been obtained either by conventional breeding, by mutagenesis or by recombinant DNA techniques. They may take the form of varieties, biotypes or genotypes.

The treatment according to the invention may also result in superadditive ("synergistic") effects, depending on the plant species or plant varieties, their location and their growth conditions (soils, climate, vegetation period, nutrition). Thus, for example, reduced application rates and/or a widened spectrum of action and/or a more potent action of the substances and compositions which can be used according to the invention, better plant growth, increased tolerance to high or low temperatures, increased tolerance to drought or to the salt content in water or soil, better flowering, facilitated harvesting, earlier ripening, higher yields, higher quality and/or higher nutritional value of the harvested products, better shelf life and/or processing of the harvested products are possible, with all these exceeding the effects actually to be expected.

The preferred transgenic plants or plant varieties (which have been obtained by genetic engineering) to be treated in accordance with the invention include all plants which obtained, by this modification owing to genetic engineering, genetic material imparting to these plants especially advantageous valuable traits. Examples of such traits are better plant growth, increased tolerance to high or low temperatures, increased tolerance to drought or to the salt content in water or soil, better flowering, facilitated harvesting, earlier ripening, higher yields, higher quality and/or higher nutritional value of the harvested products, better shelf life and/or processing of the harvested products. Other examples of such properties which are especially emphasized are an increased resistance of the plants to animal and microbial pests, such as to insects, mites, phytopathogenic fungi, bacteria and/or viruses, and an increased tolerance of the plants to certain herbicidal active compounds. Examples of transgenic plants which are mentioned are the important crop plants cereals (wheat, rice), maize, soya, potatoes, cotton, oilseed rape and fruit plants (with the fruits apples, pears, citrus fruit and grapes), with particular emphasis on maize, soya, potatoes, cotton and oilseed rape. Traits which are particularly emphasized are the increased resistance of the plants to insects by toxins formed in the plants, in particular those which are generated in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and their combinations) ("Bt plants" hereinbelow). Traits which are also particularly emphasized are the increased resistance of plants to fungi, bacteria and viruses by systemic acquired resistance (SAR), systemin, phytoalexins, elicitors and resistance genes and correspondingly expressed proteins and toxins. Other traits which are particularly emphasized are the increased tolerance of the plants to specific herbicidal active compounds, for example imidazolinones, sulphonylureas, glyphosate or phosphinothricin (for example "PAT" gene). The genes imparting the desired traits in each case can also be present in the transgenic plants in combinations with each other. Examples of "Bt plants" which may be mentioned are maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties, soya varieties which are sold under the trade names Roundup Ready® (tolerance to glyphosate, for example maize, cotton, soya), Liberty Link® (tolerance to phosphinotricin, for example oilseed rape), IMI® (tolerance to imidazolinones) and STS® (tolerance to sulphonylureas, for example maize). Other herbicide-resistant plants (bred conventionally for herbicide tolerance) which may be mentioned are also those varieties (for example maize) which are sold under the name Clearfield®. Naturally, these statements also apply to plant varieties which have these genetic traits, or genetic traits developed in the future, and which will be developed in the future or offered for sale in the future.

The plants stated can be treated especially advantageously in accordance with the invention with the compounds of the formula (I). The preferred ranges stated hereinabove for the active compounds also apply to the treatment of these plants. The treatment of plants with the compounds mentioned specifically in the present text is particularly emphasized.

The active compounds can be converted into the customary formulations such as solutions, emulsions, wettable powders, suspensions, powders, dusts, pastes, soluble powders, granules, suspoemulsion concentrates, natural and synthetic materials impregnated with active compound, and microencapsulations in polymeric materials.

These formulations are produced in the known fashion, for example by mixing the active compounds with extenders, that is liquid solvents and/or solid carriers, optionally with the use of surfactants, that is to say emulsifiers and/or dispersants and/or foam formers.

In the case of the use of water as extender, organic solvents can, for example, also be used as cosolvents. The following liquid solvents are essentially suitable: aromatics such as xylene, toluene or alkylnaphthalenes, chlorinated aromatic or chlorinated aliphatic hydrocarbons, such as chlorobenzenes, chloroethylenes or methylene chloride, aliphatic hydrocarbons such as cyclohexane or paraffins, for example, mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide and water.

Solid carriers which are suitable are:

for example ammonium salts and ground natural minerals such as kaolins, clays, talc, chalk, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic materials such as sawdust, coconut shells, maize stalks and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dystuffs and metal phthalocyanine dyestuffs, and trace nutrients such as salts of iron, manganese, boron, copper, cobalt, molybdenum and zinc.

In general, the formulations comprise between 0.1 and 95% by weight of active compound, preferably between 0.5 and 90%.

In its commercially available formulations and in the use forms prepared from these formulations, the active compound according to the invention can be present as a mixture with other active compounds such as insecticides, attractants, sterilants, bactericides, acaricides, nematicides, fungicides, growth regulators or herbicides. The insecticides include, for example, phosphoric esters, carbamates, carboxylic esters, chlorinated hydrocarbons, phenylureas, substances produced by microorganisms, others.

Examples of particularly suitable components in mixtures are the following:

Fungicides aldimorph, ampropylfos, ampropylfos-potassium, andoprim, anilazin, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, chinomethionat (quinomethionate), chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimole, etridiazole, famoxadon, fenapanil, fenarimol, fenbuconazole, fenfuram, fenitropan, fenpiclonil, fenpropidin, fenpropimorph, fentine acetate, fentine hydroxide, ferbam, ferimzone, fluazinam, flumetover, fluoromid, fluquinconazole, flurprimidol, flusilazol, flusulfamid, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatin, hexachlorobenzene, hexaconazole, hymexazole, imazalil, imibenconazole, iminoctadine, iminoctadine-albesilate, iminoctadine-triacetate, iodocarb, ipconazole, iprobenfos (IBP), iprodione, irumamicin, isoprothiolan, isovaledione, kasugamycin, kresoxim-methyl, copper preprations such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidon, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazen, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamid, tricyclazole, tridemorph, triflumizole, triforin, triticonazole, uniconazole, validamycin A, vinclozolin, viniconazol, zarilamid, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorphenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulfonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol(OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl)-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methaneamine, 8-hydroxyquinoline sulphate, 9H-xanthene-9-carboxylic acid 2-[(phenylamino)-carbonyl]-hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium hydrogencarbonate, sodium methanetetrathiolate, methyl 1-(2,3-dihydro-2,2-dimethyl-1H-inden-1-y)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidineamine, N-(4-hexylphenyl)-1,4,5,6-tetrahydro-2-pyrimidineamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methaneimidamide, sodium N-formyl-N-hydroxy-DL-alaninate, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran]-3'-one, Bactericides
  bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides
  abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusate-sodium, dofenapyn, eflusilanate, emamectin, empenthrin, endosulfan, Entomophthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

N-[2-benzoyl-1-(1,1-dimethylethyl)]-benzohydrazide, 2,2-dimethyl-3-(2,4-dichlorophenyl)-2-oxo-1-oxaspiro[4.5]dec-3-en-4-yl butanoate, N-[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

A mixture with other known active compounds, such as herbicides, or with fertilizers and growth regulators, is also possible.

When used as insecticides, the active compounds according to the invention, in their commercially available formulations and in the use forms prepared from these formulations, can furthermore be present as a mixture with synergists. Synergists are compounds by means of which the action of the active compounds is increased without it being necessary for the synergist added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

They are applied in a customary manner adapted to suit the use forms.

When applied against hygiene and stored-product pests, the active compound is distinguished by outstanding residual action on wood and clay and by good stability to alkali on limed substrates.

The active compounds according to the invention act not only against plant pests, hygiene pests and stored-product pests, but also, in the veterinary medicine sector, against animal parasites (ectoparasites) such as hard ticks, soft ticks, scab mites, harvest mites, flies (stinging and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) und Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalos, rabbits, chickens, turkeys, ducks, geese, honeybees, other domestic animals, such as, for example, dogs, cats, caged birds, aquarium fish, and what are known as experimental animals such as, for example, hamsters, guinea pigs, rats and mice. By controlling these arthropods, it is intended to reduce deaths and reduced performance (in the case of meat, milk, wool, hides, eggs, honey and the like), so that more economical and simpler animal keeping is made possible by using the active compounds according to the invention.

In the veterinary sector, the active compounds according to the invention are applied in the known manner by enteral administration in the form of, for example, tablets, capsules, drinks, drenches, granules, pastes, boluses, the feed-through method, suppositories, by parenteral administration such as, for example, by injections (intramuscular, subcutaneous, intravenous, intraperitoneal and the like), implants, by nasal application, by dermal administration in the form, for example, of dipping, spraying, pouring-on and spotting-on, washing, dusting, and with the aid of active-compound-containing shaped articles such as collars, ear tags, tail tags, limb bands, halters, marking devices and the like.

When applied to livestock, poultry, domestic animals and the like, the active compounds of the formula (I) can be applied in the form of formulations (for example powders, emulsions, flowables), which comprise the active compounds in an amount of 1 to 80% by weight, either directly or after 100- to 10,000-fold dilution, or else the active compounds can be used in the form of a medicinal bath.

Furthermore, it has been found that the compounds according to the invention show a potent insecticidal action against insects which destroy industrial materials.

The following insects may be mentioned by way of example and by preference, but without limitation:

Beetles, such as
  *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec., Tryptodendron spec., *Apate monachus, Bostrychus capucins, Heterobostrychus brunneus,* Sinoxylon spec., *Dinoderus minutus.*

Dermapterans such as
  *Sirex juvencus, Urocerus gigas, Urocerus gigas taignus, Urocerus augur.*

Termites such as
  *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails such as *Lepisma saccharina.*

Industrial materials are to be understood in the present context as meaning non-living materials, such as, preferably, polymers, adhesives, glues, paper and board, leather, wood, timber products and paints.

The material which is to be protected from insect attack is very especially preferably wood and timber products.

Wood and timber products which can be protected by the agent according to the invention, or mixtures comprising it, are to be understood as meaning, for example, construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compounds can be used as such, in the form of concentrates or generally customary formulations, such as powders, granules, solutions, suspensions, emulsions or pastes.

The abovementioned formulations can be prepared in a manner known per se, for example by mixing the active compounds with at least one solvent or diluent, emulsifier, dispersant and/or binder and fixative, water repellent, if desired, desiccants and UV stabilizers and, if desired, colorants and pigments and other processing auxiliaries.

The insecticidal compositions or concentrates used for the protecting wood and timber products contain the active compound according to the invention in a concentration of 0.0001 to 95% by weight, especially 0.001 to 60% by weight.

The amount of the compositions or concentrates employed depends on the species and the abundance of the insects and on the medium. The optimal quantity to be employed can be determined in each case by test series upon application. In general, however, it will sufficient to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organic chemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number above 35 and a flashpoint of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils which are advantageously used are those with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flashpoint above 30° C., preferably above 45° C., can be replaced in part by organochemical solvents of high or medium volatility, with the proviso that the solvent mixture also has an evaporation number above 35 and a flashpoint of above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters and the like.

Organochemical binders for the purposes of the present invention are the synthetic resins and/or binding drying oils which are known per se and which can be diluted in water and/or dissolved or dispersed or emulsified in the organochemical solvents employed, in particular binders composed of or containing an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Bitumen or bituminous substances may also be used as binders, in an amount of up to 10% by weight. In addition, colorants, pigments, water repellents, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or a plasticizer (mixture). These additives are intended to prevent volatilization of the active compounds, and also crystallization or precipitation. They preferably replace 0.01 to 30% of the binder (based on 100% of the binder employed).

The plasticizers are from the chemical classes of phthalic acid esters, such as dibutyl phthalate, dioctyl phthalate or benzyl butyl phthalate, phosphoric esters, such as tributyl phosphate, adipic esters, such as di-(2-ethylhexyl) adipate, stearates such as butyl stearate or amyl stearate, oleates, such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones, such as benzophenone and ethylenebenzophenone.

Other suitable solvents or diluents are, in particular, also water, if appropriate as a mixture with one or more of the abovementioned organochemical solvents or diluents, emulsifiers and dispersants.

Particularly effective timber protection is achieved by industrial-scale impregnating processes, such as vacuum, double vacuum or pressure processes.

If appropriate, the ready-to-use compositions can also contain further insecticides and, if appropriate, also one or more fungicides.

Additional components which may be admixed are preferably the insecticides and fungicides mentioned in WO 94/29 268. The compounds mentioned in this document are expressly part of the present application.

Very especially preferred components which may be admixed can be insecticides such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiaclopoid, methoxyphenoxide and triflumuron, and fungicides such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can simultaneously be employed for protecting against fouling objects which come into contact with salt water or brackish water, such as hulls, screens, nets, buildings, moorings and signalling systems.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus oder Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., fouling by sessile Entomostraka groups, under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, the use of heavy metals such as, for example, in bis(trialkyltin) sulfides, tri-n-butyltin laurate, tri-n-butyltin chloride, copper (I) oxide, triethyltin chloride, tri-n-butyl(2-phenyl-4-chlorophenoxy)-tin, tributyltin oxide, molybdenum disulfide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylenebisthiocarbamate, zinc oxide, copper (I) ethylene-bisdithiocarbamate, copper thiocyanate, copper naphthenate and tributyltin halides can be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable as components in combinations with the antifouling agents according to the invention are:
Algicides such as
2-tert-butylanino-4-cyclopropylamino-6-methylthio-1, 3,5-triazine, dichlorophen, diuron, endothal, fentin acetate, isoproturon, methabenzthiazuron, oxyfluorfen, quinoclamine and terbutryn;
Fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb; or conventional antifouling active compounds such as
4,5-dichloro-2-octyl -4-isothiazolin-3-one, diiodomethylparatryl sulphone, 2-(N,N-dimethylthiocarbamoylthio)-5-nitrothiazyl, potassium salts, copper salts, sodium salts and zinc salts of 2-pyridinethiol 1-oxide, pyridine-triphenylborane, tetrabutyldistannoxane, 2,3,5,6-tetrachloro-4-(methylsulphonyl)-pyridine, 2,4,5, 6-tetrachloroisophthalonitrile, tetramethylthiuram disulphide and 2,4,6-trichlorophenyl maleimide.

The antifouling compositions employed contain the compounds according to the invention in a concentration of 0.001 to 50% by weight, in particular 0.01 to 20% by weight.

Moreover, the antifouling compositions according to the invention contain the customary components such as, for example, those described in Ungerer, Chem. Ind. 1985, 37, 730–732 and Williams, Antifouling Marine Coatings, Noyes, Park Ridge, 1973.

In addition to the algicidal, fungicidal, molluscicidal active compounds and insecticidal active compounds according to the invention, antifouling paints contain, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also contain inorganic pigments, organic pigments or colorants which are preferably insoluble in water. Paints may furthermore contain materials such as colophonium to allow controlled release of the active compounds. Furthermore, the paints may contain plasticizers, modifiers which influence the rheological properties, and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests, either alone or in combination with other active compounds and auxiliaries. They are active against sensitive and resistant species and against all developmental stages. These pests include:

From the order of the Scorpionidea, for example, *Buthus occitanus*.

From the order of the Acarina, for example, *Argas persicus, Argas reflexus*, Bryobia ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus*, Polydesmus spp.

From the order of the Chilopoda, for example, Geophilus spp.

From the order of the Zygentoma, for example, Ctenolepisma spp., *Lepisma saccharina, Lepismodes inquilinus*.

From the order of the Blattaria, for example, *Blatta orientalies, Blattella germanica, Blattella asahinai, Leucophaea maderae*, Panchlora spp., Parcoblatta spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, Kalotermes spp., Reticulitermes spp.

From the order of the Psocoptera, for example, Lepinatus spp., Liposcelis spp.

From the order of the Coleptera, for example, Anthrenus spp., Attagenus spp., Dermestes spp., *Latheticus oryzae*, Necrobia spp., Ptinus spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus*, Anopheles spp., *Calliphora erythrocephala, Chrysozona pluvialis, Culex quinquefasciatus, Culex pipiens, Culex tarsalis*, Drosophila spp., *Fannia canicularis, Musca domestica*, Phlebotomus spp., *Sarcophaga carnaria*, Simulium spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis*, Paravespula spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the domestic insecticides sector, they are used alone or in combination with other suitable active compounds such as phosphoric esters, carbamates, pyrethroides, growth regulators or active compounds from other known classes of insecticides.

They are used as aerosols, pressure-free spray products, for example pump and atomizer sprays, automatic misting systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

PREPARATION EXAMPLES

Example 1

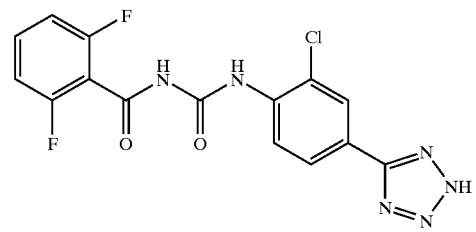

Process a

A solution of 0.95 g (5.5 mmol) of 2,6-difluorobenzoyl isocyanate in 20 ml of acetonitrile is added dropwise at room temperature to a solution of 1 g (5.5 mmol) of 5-(3-chloro-4-aminophenyl)-tetrazole in 30 ml of acetonitrile. The product which has precipitated is filtered off with suction and washed with acetonitrile.

This gives 1.1 g (53% of theory) of N-(2,6-difluorobenzoyl)-N'-(2-chloro-4-tetrazol-5-yl-phenyl)-urea with a log P(pH2) of 2.13.

Preparation of the Starting Material

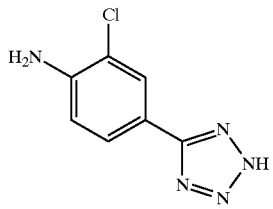
(III-1)

A mixture of 5 g (0.033 mol) of 3-chloro-4-aminobenzonitrile, 2.9 g (0.045 mol) of sodium azide, 6.2 g (0.045 mol) of triethylamine hydrochloride and 80 ml of dimethylformamide is warmed for 24 hours at 120 to 130° C. The solvent is then distilled off in vacuo, the residue is dissolved in dilute sodium hydroxide solution and the solution is acidified with dilute hydrochloric acid. The product which has precipitated is filtered off with suction and washed with water.

This gives 6.2 g (96% of theory) of 5-(3-chloro-4-aminophenyl)-tetrazole with a log P(pH2) of 1.00.

Example 2

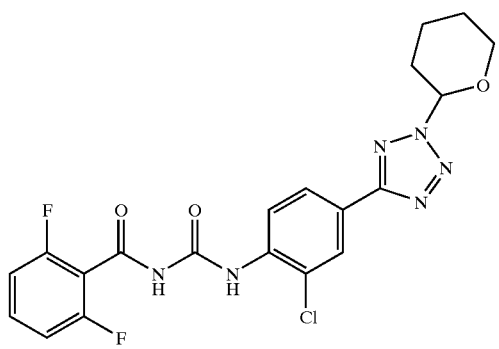

Process b

A mixture of 0.5 g (1.3 mmol) of N-(2,6-dichlorobenzoyl)-N'-(2-chloro-4-tetrazol-5-yl-phenyl)-urea [Ex. 1], 0.53 ml of 3,4-dihydro-2H-pyran and approx. 20–30 mg of p-toluenesulphonic acid in 20 ml of chloromethane is stirred overnight at room temperature. Then, the reaction mixture is extracted by shaking with 20 ml of saturated sodium bicarbonate solution and then with 20 ml of water, the organic phase is dried over sodium sulphate and this solvent is distilled off in vacuo. There remains 0.56 g (93% of theory) of N-(2,6-difluorobenzoyl)-N'-[2-chloro-4-(2-tetrahydropyran-2-yl-tetrazol-5-yl)-phenyl]-urea of log P(pH2) 3.72.

Example 3

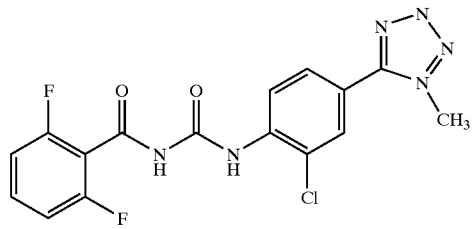

Process a

A solution of 0.26 g (1.4 mmol) of 2,6-difluorobenzoyl isocyanate in 10 ml of acetonitrile is added dropwise at room temperature to a solution of 0.3 g (1.4 mmol) 1-methyl-5-(3-chloro-4-aminophenyl)-tetrazole in 10 ml of acetonitrile. The product which has precipitated is filtered off with suction and washed with acetonitrile.

This gives 0.36 g (65% of theory) of N-(2,6-difluorobenzoyl)-N'-[2-chloro-4-(1-methyl-tetrazol-5-yl]-urea of log P(pH2) 2.31.

Preparation of the Starting Material

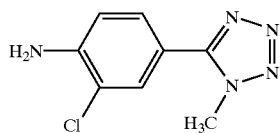
(III-2)

A mixture of 3 g (0.015 mol) of 5-(3-chloro-4-aminophenyl)-tetrazole, 2.8 g (0.02 mol) of potassium carbonate, 2.84 g (0.02 mol) of iodomethane and 50 ml of acetonitrile is stirred for 48 hours at 60° C. The solvent is then distilled off in vacuo, the residue is extracted by shaking with water and ethyl acetate, and the organic phase is separated off and dried over sodium sulphate. The solvent is distilled off in vacuo and the residue is purified by silica gel chromatography (eluant=dichloromethane: diethyl ether=11:1).

This gives 0.3 g (9.5% of theory) of 1-methyl-(3-chloro-4-aminophenyl)-tetrazole of log P (pH2) 1.17.

The compounds of the formula (I) given in Table 1 hereinbelow are obtained analogously to Examples 1 to 3 or in accordance with the general preparation instructions:

TABLE 1

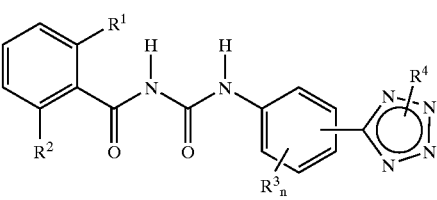
(I)

| Ex. No. | $R^1$ | $R^2$ | $R_n^3$ | Position of substitution of the tetrazole on the phenyl ring | $R^4$ | logP (pH2) or m.p. (° C.) |
|---|---|---|---|---|---|---|
| 4 | F | F | 2-Cl | 4 | 2-$C_4H_9$-t | 207 |
| 5 | F | F | 2-Cl | 4 | 2-$CH_3$ | 2.88 |
| 6 | F | F | 4-Cl | 2 | H | 2.16 |

TABLE 1-continued

Structure (I):

Ar-C(=O)-NH-C(=O)-NH-Ar'(R³ₙ)-tetrazole(R⁴), where Ar = 2,6-disubstituted phenyl (R¹, R²)

| Ex. No. | R¹ | R² | R ³ₙ | Position of substitution of the tetrazole on the phenyl ring | R⁴ | logP (pH2) or m.p. (° C.) |
|---|---|---|---|---|---|---|
| 7 | F | F | 2,5-Cl₂ | 4 | H | 2.30 |
| 8 | F | F | 2-Cl | 4 | 2-(1-methylcyclohexyl) | 178 |
| 9 | F | F | 2-Cl | 4 | 2-CH₂-(tetrahydropyran-2-yl) | 3.71 |
| 10 | F | Cl | 2-Cl | 4 | 2-C₄H₉-t | 201 |
| 11 | F | F | 4-Cl | 2 | 2-C₄H₉-t | 4.20 |
| 12 | F | F | 2-Cl | 4 | 2-CH₂—COOCH₃ | 200 |
| 13 | F | F | 2-Cl | 4 | 2-(CH₂)₂—OCOCH₃ | 204 |
| 14 | F | F | 2-Cl | 4 | 2-CH₂OC₂H₅ | 165 |
| 15 | F | F | 2-Cl | 4 | 2-C₃H₇-n | 206 |
| 16 | F | F | 2,5-Cl₂ | 4 | 2-C₄H₉-t | 205 |
| 17 | F | F | 2-Cl | 4 | 2-CH₂—(4-Br-phenyl) | 211 |
| 18 | F | F | 2-Cl | 4 | 2-CHF₂ | 189 |
| 19 | F | F | 2-Cl | 4 | 2-phenyl | 4.63 |
| 20 | F | F | 2-Cl | 4 | 1-CHF₂ | 196 |
| 21 | F | F | 2-Cl | 4 | 2-C₄H₉-i | 219 |
| 22 | F | F | 2-Cl | 4 | 2-CH₂—CH₂—CF=CF₂ | 196 |
| 23 | F | F | 2,6-Cl₂ | 4 | 2-C₄H₉-t | 221 |
| 24 | F | F | 2,6-Cl₂ | 4 | 2-C₄H₉-i | 190 |
| 25 | F | F | 2,5-Cl₂ | 4 | 2-C₄H₉-i | 193 |
| 26 | F | F | 2,5-Cl₂ | 4 | 2-C₃H₇-n | 192 |
| 27 | F | F | — | 4 | 2-C₄H₉-t | 218 |
| 28 | F | Cl | — | 4 | 2-C₄H₉-t | 184 |
| 29 | F | F | 2,5-Cl₂ | 4 | 2-CHF₂ | 155 |
| 30 | F | F | 2-Cl₂ | 4 | 2-CH₂—C(CH₃)=CH₂ | 174 |
| 31 | Cl | H | — | 4 | 2-C₄H₉-t | 218 |
| 32 | Cl | H | 2-Cl | 4 | 2-C₄H₉-t | 184 |
| 33 | Cl | H | 2,6-Cl₂ | 4 | 2-C₄H₉-t | 203 |
| 34 | Cl | H | 2,5-Cl₂ | 4 | 2-C₄H₉-t | 211 |
| 35 | F | F | 3-Cl | 4 | 2-C₄H₉-t | 3.68 |
| 36 | Cl | H | 3-Cl | 4 | 2-C₄H₉-t | 198 |
| 37 | F | F | 3-F | 4 | 2-C₄H₉-t | 218 |
| 38 | Cl | H | 3-F | 4 | 2-C₄H₉-t | 221 |
| 39 | F | F | 2,6-F₂ | 4 | 2-C₄H₉-t | 226 |
| 40 | Cl | H | 2,5-F₂ | 4 | 2-C₄H₉-t | 227 |
| 41 | F | F | 2,5-F₂ | 4 | 2-C₄H₉-t | 199 |
| 42 | Cl | H | 2,6-F₂ | 4 | 2-C₄H₉-t | 215 |

TABLE 1-continued

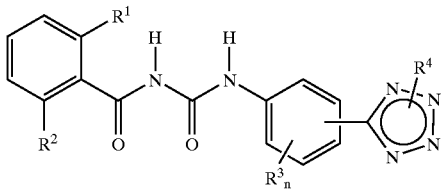

(I)

| Ex. No. | R¹ | R² | $R_n^3$ | Position of substitution of the tetrazole on the phenyl ring | R⁴ | logP (pH2) or m.p. (° C.) |
|---|---|---|---|---|---|---|
| 43 | F | F | 2,5-Cl₂ | 4 | $-C(CH_3)(CH_2CH_3)(CH_2CH_3)$ | 204 |
| 44 | F | F | 2,5-Cl₂ | 4 | $-C(CH_3)(CH_2CH_3)(CH_2CH_3)$ | 216 |
| 45 | F | F | — | 4 | 2-C(C₂H₅)₂CH₃ | 193 |
| 46 | F | F | — | 4 | 2-C(CH₃)₂C₂H₅ | 191 |
| 47 | F | F | 2-F | 4 | 2-C(C₂H₅)₂CH₃ | 185 |
| 48 | F | F | 2-F | 4 | 2-C(CH₃)₂C₂H₅ | 209 |
| 49 | Cl | H | — | 4 | 2-C(CH₃)₂C₂H₅ | 197 |
| 50 | Cl | H | — | 4 | 2-C(C₂H₅)₂CH₃ | 179 |
| 51 | F | Cl | — | 4 | 2-C(CH₃)₂C₂H₅ | 189 |
| 52 | F | Cl | — | 4 | 2-C(C₂H₅)₂CH₃ | 191 |
| 53 | F | F | 3,5-F₂ | 4 | 2-C₄H₉-t | 216 |
| 54 | F | F | 2,3-F₂ | 4 | 2-C₄H₉-t | 202 |
| 55 | Cl | H | 2,3-F₂ | 4 | 2-C₄H₉-t | 213 |
| 56 | F | F | 2-F | 4 | 2-C₄H₉-t | 213 |
| 57 | Cl | H | 2-F | 4 | 2-C₄H₉-t | 209 |
| 58 | F | F | 3,5-Cl₂ | 4 | 2-C₄H₉-t | 192 |
| 59 | Cl | H | 3,5-Cl₂ | 4 | 2-C₄H₉-t | 176 |
| 60 | F | F | 2,3-Cl₂ | 4 | 2-C₄H₉-t | 164 |
| 61 | Cl | H | 2,3-Cl₂ | 4 | 2-C₄H₉-t | 126 |
| 62 | Cl | H | 2-Cl | 4 | 2-CHF₂ | 181 |
| 63 | Cl | H | 2-Cl | 4 | 1-CHF₂ | 193 |
| 64 | F | F | — | 4 | 2-CHF₂ | 186 |
| 65 | Cl | H | — | 4 | 2-CHF₂ | 168 |
| 66 | Cl | H | — | 4 | 1-CHF₂ | 180 |
| 67 | F | F | — | 4 | 1-CHF₂ | 214 |
| 68 | Cl | H | 2,5-Cl₂ | 4 | 2-CHF₂ | 158 |
| 69 | F | F | 3-Cl | 4 | 2-CHF₂ | 172 |
| 70 | Cl | H | 3-Cl | 4 | 2-CHF₂ | 163 |

TABLE 1-continued

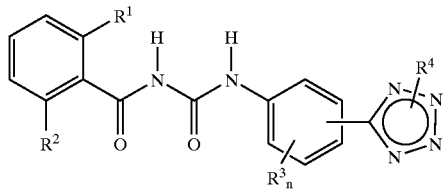

(I)

| Ex. No. | R¹ | R² | R$_n^3$ | Position of substitution of the tetrazole on the phenyl ring | R⁴ | logP (pH2) or m.p. (° C.) |
|---|---|---|---|---|---|---|
| 71 | F | F | 3-F | 4 | 2-CHF$_2$ | 194 |
| 72 | F | F | — | 3 | 2-C$_4$H$_9$-t | 188 |
| 73 | Cl | H | — | 3 | 2-C$_4$H$_9$-t | 164 |
| 74 | F | F | — | 3 | H | |
| 75 | Cl | H | — | 3 | H | |
| 76 | F | F | — | 3 | 2-CHF$_2$ | 169 |
| 77 | Cl | H | — | 3 | 2-CHF$_2$ | |
| 78 | F | F | — | 3 | 1-CHF$_2$ | 189 |
| 79 | Cl | H | — | 3 | 1-CHF$_2$ | |
| 80 | F | F | 4-Cl | 3 | 2-C$_4$H$_9$-t | |
| 81 | Cl | H | 4-Cl | 3 | 2-C$_4$H$_9$-t | |
| 82 | F | F | 4-Cl | 3 | 2-CHF$_2$ | |
| 83 | Cl | H | 4-Cl | 3 | 2-CHF$_2$ | |
| 84 | Cl | H | 4-Cl | 3 | 1-CHF$_2$ | |
| 85 | F | F | 4-Cl | 3 | 1-CHF$_2$ | |
| 86 | F | F | 5-CF$_3$ | 3 | 2-C$_4$H$_9$-t | |
| 87 | Cl | H | 5-CF$_3$ | 3 | 2-C$_4$H$_9$-t | |
| 88 | F | F | 5-CF$_3$ | 3 | 2-CHF$_2$ | |
| 89 | Cl | H | 5-CF$_3$ | 3 | 2-CHF$_2$ | |
| 90 | F | F | 5-CF$_3$ | 3 | 1-CHF$_2$ | |
| 91 | Cl | H | 5-CF$_3$ | 3 | 1-CHF$_2$ | |
| 92 | F | F | 6-Cl— | 3 | 2-C$_4$H$_9$-t | |
| 93 | Cl | H | 6-Cl— | 3 | 2-C$_4$H$_9$-t | |
| 94 | F | F | 6-Cl— | 3 | 2-CHF$_2$ | |
| 95 | Cl | H | 6-Cl— | 3 | 2-CH$_2$ | |
| 96 | F | F | 6-Cl— | 3 | 1-CHF$_2$ | |
| 97 | Cl | H | 6-Cl— | 3 | 1-CHF$_2$ | |

Preparation of Further Starting Materials of the Formula (III)

Example a

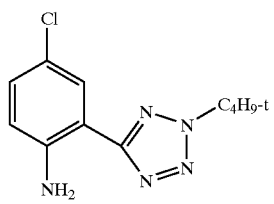

(III-3)

1.6 ml of concentrated sulphuric acid is added to a mixture of 5 g of (0.026 mol) of 5-(2-amino-5-chlorophenyl)-tetrazole, 6.5 ml of tert-butanol and 32 ml of trifluoroacetic acid. The reaction mixture is stirred overnight, the solvent is then distilled off in vacuo, and the residue is treated with saturated sodium bicarbonate solution. The product is extracted in ethyl acetate. The organic phase is dried over sodium sulphate and the solvent is then distilled off in vacuo.

This gives 5.2 g (80% of theory) of 5-(2-amino-5-chlorophenyl)-2-tert-butyl-tetrazole of log P(pH2) 3.58.

Example b

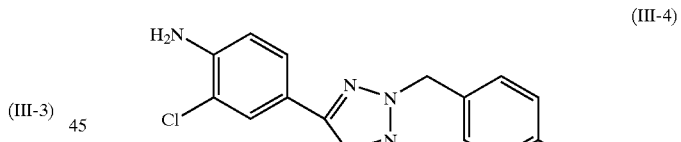

(III-4)

A mixture of 1 g (5 mmol) of 5-(3-chloro-4-aminophenyl)-tetrazole, 1.37 g (5.5 mmol) of 4-bromobenzyl bromide, 0.76 g (5.5 mmol) of potassium carbonate and 30 ml of acetonitrile is warmed for 18 hours at 50 to 60° C. The solvent is then distilled off in vacuo, and the residue is extracted by shaking with water and ethyl acetate. The organic phase is separated off, dried over sodium sulphate and evaporated to dryness in vacuo.

This gives 1.8 g (99% of theory) of 5-(3-chloro-4-aminophenyl)-2-(4-bromobenzyl)-tetrazole of log P (pH2) 3.52.

The compounds of the formula (III) given in Table 2 hereinbelow are obtained analogously to Examples 1, 3a and 3b:

TABLE 2

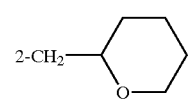

(III)

| Ex. No. | $R_n^3$ | Position of substitution of the tetrazole on the phenyl ring | $R^4$ | logP (pH2) |
|---|---|---|---|---|
| III-5 | 2-Cl, 6-CH$_3$ | 4 | H | 1.20 |
| III-6 | 2-Cl | 4 | 2-CH$_3$ | 1.70 |
| III-7 | 4-Cl | 2 | H | 1.50 |
| III-8 | 2,5-Cl$_2$ | 4 | H | 1.16 |
| III-9 | 3-Cl | 4 | H | 1.53 |
| III-10 | 2-Cl | 4 | 2-CH$_2$COOCH$_3$ | 1.92 |
| III-11 | 2-Cl | 4 | 2-CH$_2$OC$_2$H$_5$ | 2.34 |
| III-12 | 2-Cl | 4 | 2-C$_3$H$_7$-n | 2.52 |
| III-13 | 2-Cl | 4 | 2-CH$_2$-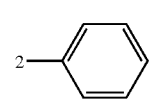 | 2.59 |
| III-14 | 2-Cl | 4 | 2-CHF$_2$ | 2.08 |
| III-15 | 2-Cl | 4 | 2- | 3.28 |
| III-16 | 2-Cl | 4 | 1-CHCF$_2$ | 1.92 |
| III-17 | 2-Cl | 4 | 2-C$_4$H$_9$-i | 2.95 |
| III-18 | 2-Cl | 4 | 2-CH$_2$—CH$_2$—CF=CF$_2$ | 2.68 |
| III-19 | 2,6-Cl$_2$ | 4 | 2-C$_4$H$_9$-t | 3.81 |
| III-20 | 2,6-Cl$_2$ | 4 | 2-C$_4$H$_9$-i | 3.78 |
| III-21 | 2,5-Cl$_2$ | 4 | 2-C$_4$H$_9$-i | 3.15 |
| III-22 | 2,5-Cl$_2$ | 4 | 2-C$_3$H$_7$-n | 2.75 |
| III-23 | — | 4 | 2-C$_4$H$_9$-t | 1.69 |
| III-24 | 2-Cl | 4 | 2-CH$_2$—CH$_2$—OCOCH3 | 1.92 |
| III-25 | 2,6-Cl$_2$ | 4 | H | 1.40 |
| III-26 | 2-Cl | 4 | 2-C$_4$H$_9$-t | 2.94 |
| III-27 | 2,5-Cl$_2$ | 4 | 2-C$_4$H$_9$-t | |
| III-28 | 2,5-Cl$_2$ | 4 | 2-CHF$_2$ | 2.69 |
| III-29 | 2,5-Cl$_2$ | 4 | 1-CHF$_2$ | 2.36 |
| III-30 | 2-Cl | 4 | 1-CHF$_2$ | 1.92 |
| III-31 | 3-Cl | 4 | 2-C$_4$H$_9$-t | 2.42 |
| III-32 | 3-F | 4 | 2-C$_4$H$_9$-t | 2.14 |
| III-33 | 2,6-F$_2$ | 4 | 2-C$_4$H$_9$-t | |
| III-34 | 2,5-F$_2$ | 4 | 2-C$_4$H$_9$-t | |
| III-35 | 2,5-Cl$_2$ | 4 | 2-C(C$_2$H$_5$)$_2$\|CH$_3$ | |
| III-36 | 2,5-Cl$_2$ | 4 | 2-C(CH$_3$)$_2$\|C$_2$H$_5$ | |
| III-37 | — | 4 | 2-C(C$_2$H$_5$)$_2$\|CH$_3$ | |
| III-38 | — | 4 | 2-C(CH$_3$)$_2$\|C$_2$H$_5$ | |
| III-39 | 3-F | 4 | 2-C(C$_2$H$_5$)$_2$\|CH$_3$ | |
| III-40 | 3-F | 4 | 2-C(CH$_3$)$_2$\|C$_2$H$_5$ | |
| III-41 | 3,5-F$_2$ | 4 | 2-C$_4$H$_9$-t | |
| III-42 | 2,3-F$_2$ | 4 | 2-C$_4$H$_9$-t | |
| III-43 | 2-F | 4 | 2-C$_4$H$_9$-t | |
| III-44 | 3,5-Cl$_2$ | 4 | 2-C$_4$H$_9$-t | |
| III-45 | 2,3-Cl$_2$ | 4 | 2-C$_4$H$_9$-t | |
| III-46 | — | 4 | 2-CHF$_2$ | 1.49 |
| III-47 | — | 4 | 1-CHF$_2$ | 1.24 |
| III-48 | 3-Cl | 4 | 2-CHF$_2$ | 2.09 |
| III-49 | 3-Cl | 4 | 1-CHF$_2$ | 1.81 |
| III-50 | 3-F | 4 | 2-CHF$_2$ | 1.84 |
| III-51 | — | 3 | H | |
| III-52 | — | 3 | 2-C$_4$H$_9$-t | |
| III-53 | — | 3 | 2-CHF$_2$ | |
| III-54 | — | 3 | 1-CHF$_2$ | |
| III-55 | 4-Cl | 3 | 2-C$_4$H$_9$-t | |
| III-56 | 4-Cl | 3 | 2-CHF$_2$ | |
| III-57 | 4-Cl | 3 | 1-CHF$_2$ | |
| III-58 | 5-CF$_3$ | 3 | 2-C$_4$H$_9$-t | |
| III-59 | 5-CF$_3$ | 3 | 2-CHF$_2$ | |
| III-60 | 5-CF$_3$ | 3 | 1-CHF$_2$ | |
| III-61 | 6-Cl | 3 | 2-C$_4$H$_9$-t | |
| III-62 | 6-Cl | 3 | 2-CHF$_2$ | |
| III-63 | 6-Cl | 3 | 1-CHF$_2$ | |

The logP values were determined as stipulated in EEC directive 79/831 Annex V. A8 by HPLC (gradient method, acetonitrile/0.1% aqueous phosphoric acid).

USE EXAMPLES

Example A

*Heliothis virescens* Test

| | |
|---|---|
| Solvent: | 30 parts by weight of dimethylformamide |
| Emulsifier: | 1 part by weight of alkylaryl polyglycol ether |

To produce a suitable active compound preparation, 1 part by weight of active compound is mixed with the stated amounts of solvent and emulsifier, and the concentrate is diluted with emulsifier-containing water to the desired concentration.

Soya shoots (*Glycine max*) are treated by dipping into the active compound preparation of the desired concentration and are populated with *Heliothis virescens* while the leaves are still moist.

After the desired period, the destruction is determined in %. 100% means that all the caterpillars have been killed; 0% means that none of the caterpillars have been killed.

In this test, a destruction of 100% is shown, after 6 days, at an exemplary active compound concentration of 0.1% of, for example, the compound of Preparation Example 4.

Example B

*Phaedon larvae* Test

| Solvent: | 30 parts by weight of dimethylformamide |
|---|---|
| Emulsifier: | 1 part by weight of alkylaryl polyglycol ether |

To produce a suitable active compound preparation, 1 part by weight of active compound is mixed with the stated amounts of solvent and emulsifier, and the concentrate is diluted with emulsifier-containing water to the desired concentration.

Cabbage leaves (*Brassica oleracea*) are treated by dipping into the active compound preparation of the desired concentration and are populated with mustard beetle (*Phaedon cochleariae*) larvae while the leaves are still moist.

After the desired period, the destruction is determined in %. 100% means that all the beetle have been killed; 0% means that none of the beetle larvae have been killed.

In this test, a destruction of 100% is shown, after 7 days, at an exemplary active compound concentration of 0.1% of, for example, the compounds of Preparation Examples 4, 10, 16, 18 and 20.

Example C

Plutella Test

| Solvent: | 30 parts by weight of dimethylformamide |
|---|---|
| Emulsifier: | 1 part by weight of alkylaryl polyglycol ether |

To produce a suitable active compound preparation, 1 part by weight of active compound is mixed with the stated amounts of solvent and emulsifier, and the concentrate is diluted with emulsifier-containing water to the desired concentration.

Cabbage leaves (*Brassica oleracea*) are treated by dipping into the active compound preparation of the desired concentration and are populated with diamond-back moth (*Plutella xylostella*) caterpillars while the leaves are still moist.

After the desired period, the destruction is determined in %. 100% means that all the caterpillars have been killed; 0% means that none of the caterpillars have been killed.

In this test, a destruction of 100% is shown, after 6 days, at an exemplary active compound concentration of 0.1% of, for example, the compound of Preparation Example 4.

Example D

*Spodoptera exigua* Test

| Solvent: | 30 parts by weight of dimethylformamide |
|---|---|
| Emulsifier: | 1 part by weight of alkylaryl polyglycol ether |

To produce a suitable active compound preparation, 1 part by weight of active compound is mixed with the stated amounts of solvent and emulsifier, and the concentrate is diluted with emulsifier-containing water to the desired concentration.

Cabbage leaves (*Brassica oleracea*) are treated by dipping into the active compound preparation of the desired concentration and are populated with fall armyworm (*Spodoptera exigua*) caterpillars while the leaves are still moist.

After the desired period, the destruction is determined in %. 100% means that all the caterpillars have been killed; 0% means that none of the caterpillars have been killed.

In this test, a destruction of 100% is shown, after 6 days, at an exemplary active compound concentration of 0.1% of, for example, the compound of Preparation Example 4.

Example E

*Spodoptera frugiperda* Test

| Solvent: | 30 parts by weight of dimethylformamide |
|---|---|
| Emulsifier: | 1 part by weight of alkylaryl polyglycol ether |

To produce a suitable active compound preparation, 1 part by weight of active compound is mixed with the stated amounts of solvent and emulsifier, and the concentrate is diluted with emulsifier-containing water to the desired concentration.

Cabbage leaves (*Brassica oleracea*) are treated by dipping into the active compound preparation of the desired concentration and are populated with fall armyworm (*Spodoptera frugiperda*) caterpillars while the leaves are still moist.

After the desired period, the destruction is determined in %. 100% means that all the caterpillars have been killed; 0% means that none of the caterpillars have been killed.

In this test, a destruction of 100% is shown, after 7 days, at an exemplary active compound concentration of 0.1% of, for example, the compound of Preparation Examples 4, 5, 10 14, 15, 16, 18 and 20.

Example F

Limit Concentration Test/soil-dwelling Insects: Treatment of Transgenic Plants

Test insect: *Diabrotica balteata* larvae in the soil

| Solvent: | 7 parts by weight of [lacuna] |
|---|---|
| Emulsifier: | 1 part by weight of alkylaryl polyglycol ether |

To prepare a suitable preparation of active compound, 1 part by weight of active compound is mixed with the stated amount of solvent, the stated amount of emulsifier is added, and the concentrate is diluted with water to the desired concentration.

The active compound preparation is poured onto the soil. The concentration of the active compound in the preparation is of virtually no importance, only the amount of active compound by weight per unit volume of soil, which is stated in ppm (mg/l), being decisive. The soil is filled into 0.25 l pots and these are left to stand at 20° C.

Immediately after setting up the experiment, 5 pregerminated maize kernels cv. YIELD GUARD (trade mark of Monsanto Comp., USA) are placed into each pot. After 2 days, the test insects in question are placed into the treated soil. After a further 7 days, the efficacy of the active compound is determined by counting the maize plants which have emerged (1 plant=20% action).

Example G
*Heliothis virescens* Test: Treatment of Transgenic Plants

| | |
|---|---|
| Solvent: | 7 parts by weight of [lacuna] |
| Emulsifier: | 1 part by weight of alkylaryl polyglycol ether |

To prepare a suitable preparation of active compound, 1 part by weight of active compound is mixed with the stated amount of solvent, the stated amount of emulsifier is added, and the concentrate is diluted with water to the desired concentration.

Soya shoots (*Glycine max*) cv. Roundup Ready (trade mark of Monsanto Comp. USA) are treated by dipping into the active compound preparation of the desired concentration and populated with the tobacco budworm (*Heliothis virescens*) while the leaves are still moist.

After the desired time, the destruction of the insects is determined.

What is claimed is:

1. A compound of the formula (I)

(I)

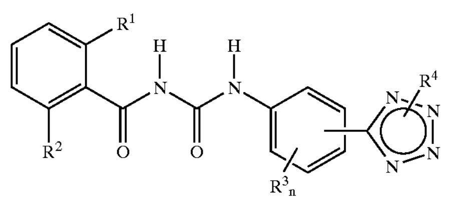

wherein $R^1$ represents halogen, $R^2$ represents hydrogen or halogen, $R^3$ represents halogen, alkyl or halogenoalkyl, n represents 0, 1 or 2 and $R^4$ represents hydrogen, optionally substituted alkyl, optionally substituted alkenyl, alkoxyalkyl, alkoxycarbonylalkyl, alkylcarbonyloxyalkyl, alkylsulphonyl, diaminocarbonyl; in each case optionally substituted aryl, arylalkyl or arylsulphonyl; in each case optionally substituted cycloalkyl or cycloalkylalkyl or in each case optionally substituted heterocyclyl or heterocyclylalkyl.

2. The compound of the formula (I) according to claim 1 wherein $R^1$ represents fluorine or chlorine, $R^2$ represents hydrogen, fluorine or chlorine, $R^3$ represents fluorine, chlorine, bromine, $C_1$–$C_4$-alkyl or $C_1$–$C_4$-halogenoalkyl, n represents 0, 1 or 2, and $R^4$ represents hydrogen, $C_1$–$C_6$-alkyl, $C_1$–$C_4$-halogenoalkyl, $C_2$–$C_4$-alkenyl, $C_2$–$C_4$-halogenoalkenyl, $C_1$–$C_4$-alkoxy-$C_1$–$C_4$-alkyl, $C_1$–$C_4$-alkoxy-carbonyl-$C_1$–$C_4$-alkyl, $C_1$–$C_4$-alkyl-carbonyloxy-$C_1$–$C_4$-alkyl; $C_1$–$C_4$-alkylsulphonyl, di-($C_1$–$C_4$-alkyl)-aminocarbonyl, or represents phenyl, benzyl or phenylsulphonyl, each of which is optionally monosubstituted to trisubstituted by identical or different substituents from the series consisting of halogen, nitro, cyano, $C_1$–$C_4$-alkyl, $C_1$–$C_4$-alkoxy, $C_1$–$C_4$-halogenoalkyl and $C_1$–$C_4$-halogenoalkoxy; or represents cyclopentyl, cyclohexyl or cyclohexyl-$C_1$–$C_2$-alkyl, each of which is optionally monosubstituted to trisubstituted by identical or different substituents from the series consisting of $C_1$–$C_4$-alkyl and $C_1$–$C_4$-alkoxy, or represents five- or six-membered heterocyclyl or five- or six-membered heterocyclyl-$C_1$–$C_2$-alkyl, each of which has one or two hetero atoms, such as N, O or S atoms, and each of which is optionally monosubstituted to trisubstituted by identical or different substituents from the series consisting of $C_1$–$C_4$-alkyl and $C_1$–$C_4$-alkoxy.

3. A compound of the formula (I) according to claim 1 wherein $R^1$ represents fluorine or chlorine, $R^2$ represents hydrogen, fluorine or chlorine, $R^3$ represents fluorine, chlorine, methyl or trifluoromethyl, n represents 0, 1 or 2, and $R^4$ represents hydrogen, $C_1$–$C_6$-alkyl, $C_2$–$C_4$-alkenyl, $C_1$–$C_2$-halogenoalkyl or $C_2$–$C_4$-halogenoalkenyl having in each case 1 to 3 identical or different halogen atoms from the series consisting of fluorine, chlorine and bromine; $C_1$–$C_4$-alkoxy-$C_1$–$C_2$-alkyl, $C_1$–$C_4$-alkoxy-carbonyl-$C_1$–$C_2$-alkyl, $C_1$–$C_4$-alkyl-carbonyloxy-$C_1$–$C_2$-alkyl, $C_1$–$C_2$-alkylsulfonyl, di-($C_1$–$C_2$-alkyl)-aminocarbonyl; or represents phenyl, benzyl or phenylsulphonyl, each of which is optionally monosubstituted to trisubstituted by identical or different substituents from the series consisting of halogen, nitro, cyano, $C_1$–$C_4$-alkyl, $C_1$–$C_4$-alkoxy, $C_1$–$C_2$-halogenoalkyl and $C_1$–$C_2$-halogenoalkoxy having in each case 1 to 3 identical or different halogen atoms; or represents cyclopentyl, cyclohexyl or cyclohexylmethyl, each of which is optionally monosubstituted to trisubstituted by identical or different substituents from the series consisting of $C_1$–$C_4$-alkyl and $C_1$–$C_4$-alkoxy; or represents tetrahydrofuranyl, tetrahydrofuranylmethyl, tetrahydropyranyl or tetrahydropyranylmethyl, each of which is optionally monosubstituted to trisubstituted by identical or different substituents from the series consisting of $C_1$–$C_4$-alkyl and $C_1$–$C_4$-alkoxy.

4. A compound of the formula (I) according to claim 1 wherein $R^1$ represents fluorine or chlorine, $R^2$ represents hydrogen, fluorine or chlorine, $R^3$ represents fluorine, chlorine or trifluoromethyl, n represents 0, 1 or 2, and $R^4$ represents hydrogen; methyl, ethyl, n- or i-propyl, n-, i-, s- or t-butyl; 1-ethyl-1-methyl-propyl, 1,1-dimethylpropyl, 2-methyl-2-propenyl, fluoromethyl, difluoromethyl, trifluoromethyl, 1,1-difluoroethyl, 2,2,2-trifluoroethyl, 3,4,4-trifluoro-3-butenyl, 4,4-difluoro-3-butenyl, methoxymethyl, ethoxymethyl, methoxyethyl, ethoxyethyl, methoxycarbonylmethyl, ethoxycarbonylmethyl, methoxycarbonylethyl, ethoxycarbonylethyl, methylcarbonyloxymethyl, ethylcarbonyloxymethyl, methylcarbonyloxyethyl, ethylcarbonyloxyethyl, methylsulphonyl, ethylsulphonyl, dimethylaminocarbonyl, methylethylaminocarbonyl, diethylaminocarbonyl; represents phenyl, benzyl or phenylsulphonyl, each of which is optionally monosubstituted or disubstituted by identical or different substituents from the series consisting of fluorine, chlorine, bromine, methyl, methoxy, trifluoromethyl or trifluoromethoxy; or represents cyclohexyl, tetrahydropyranyl or tetrahydropyranylmethyl, each of which is optionally monosubstituted or disubstituted by identical or different substituents from the series consisting of methyl, ethyl, methoxy or ethoxy.

5. A process for the preparation of a compound of the formula (I) according to claim 1 wherein a) a compound of the formula (II)

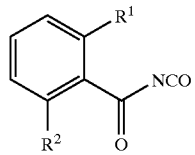

(II)

wherein $R^1$ and $R^2$ are as defined in claim 1 is reacted with a compound of the formula (III)

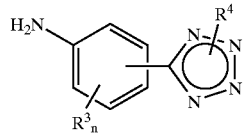

(III)

wherein $R^3$, n and $R^4$ are as defined in claim 1 in the presence of a diluent; and, b) optionally, whereupon the resulting compound of the formula (Ia)

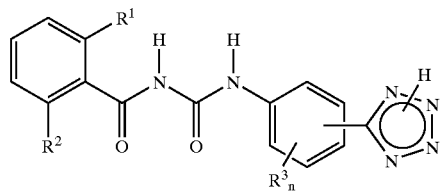

(Ia)

wherein $R^1$, $R^2$, $R^3$ and n are as defined in claim 1 is reacted with a compound of the formula (IV)

$$E—R^{4-1}$$ (IV)

wherein $R^{4-1}$ is as defined for $R^4$ in claim 1, with the exception of hydrogen, and E represents an anionic leaving group in the presence of a diluent and, optionally, in the presence of an acid acceptor.

6. A pesticidal formulation and/or a herbicidal formulation comprising at least one compound of the formula (I) according to claim 1.

7. A method of controlling one or more animal pests and/or undesired vegetation cover comprising allowing a compound of the formula (I) according to claim 1 to act on said one or more pests and/or said undesired vegetation and/or their environment.

8. A process for the preparation of one or more pesticidal formulations and/or herbicidal formulations comprising mixing one or more compounds of the formula (I) according to claim 1 with one or more extenders and/or surfactants.

* * * * *